(12) United States Patent
Leung et al.

(10) Patent No.: US 8,524,932 B2
(45) Date of Patent: Sep. 3, 2013

(54) PROCESS FOR PREPARING POROUS METAL-ORGANIC FRAMEWORKS BASED ON ALUMINUM FUMARATE

(75) Inventors: Emi Leung, Somerset, NJ (US); Ulrich Müller, Neustadt (DE); Natalia Trukhan, Ludwigshafen (DE); Hendrick Mattenheimer, Ludwigshafen (DE); Gerhard Cox, Bad Dürkheim (DE); Stefan Blei, Mannheim (DE)

(73) Assignee: BASF SE, Ludwigshafen (DE)

( * ) Notice: Subject to any disclaimer, the term of this patent is extended or adjusted under 35 U.S.C. 154(b) by 173 days.

(21) Appl. No.: 13/249,943

(22) Filed: Sep. 30, 2011

(65) Prior Publication Data

US 2012/0082864 A1    Apr. 5, 2012

Related U.S. Application Data

(60) Provisional application No. 61/387,991, filed on Sep. 30, 2010.

(51) Int. Cl.
*C07F 5/06* (2006.01)
(52) U.S. Cl.
USPC ............ 556/183; 556/170; 556/181; 556/182
(58) Field of Classification Search
None
See application file for complete search history.

(56) References Cited

U.S. PATENT DOCUMENTS

| 2008/0281116 | A1 | 11/2008 | Schubert et al. |
| 2009/0092818 | A1 | 4/2009 | Kiener et al. |
| 2010/0166644 | A1 | 7/2010 | Schubert et al. |
| 2012/0055880 | A1* | 3/2012 | Loiseau et al. ................ 210/660 |

FOREIGN PATENT DOCUMENTS

| CN | 101429209 | 5/2009 |
| EP | 1070538 | 1/2001 |
| EP | 1785428 | 5/2007 |
| WO | WO-03/102000 | 12/2003 |
| WO | WO-2007/023134 | 3/2007 |
| WO | WO 2007/118841 | 10/2007 |
| WO | WO-2010/058123 | 5/2010 |

OTHER PUBLICATIONS

"Machine Translation of EP1785428", May 16, 2007, 15 pages.
"International Search Report of PCT/IB2011/053892", mailed on Jan. 19, 2012, 4 pages.

* cited by examiner

*Primary Examiner* — Sudhakar Katakam
(74) *Attorney, Agent, or Firm* — Servilla Whitney LLC

(57) ABSTRACT

The present invention relates to a process for preparing a porous metal-organic framework comprising at least one at least bidentate organic compound coordinated to at least one metal ion, where the at least one metal ion is based on an aluminum ion and the at least one at least bidentate organic compound is based on fumaric acid, by reacting at least one aluminum compound with at least fumaric acid in an alkaline aqueous medium, optionally in the presence of at least one base, at a temperature in the range from 20° C. to 100° C. at an absolute pressure of not more than 2 bar for from 0.2 to 4 hours.

16 Claims, 1 Drawing Sheet

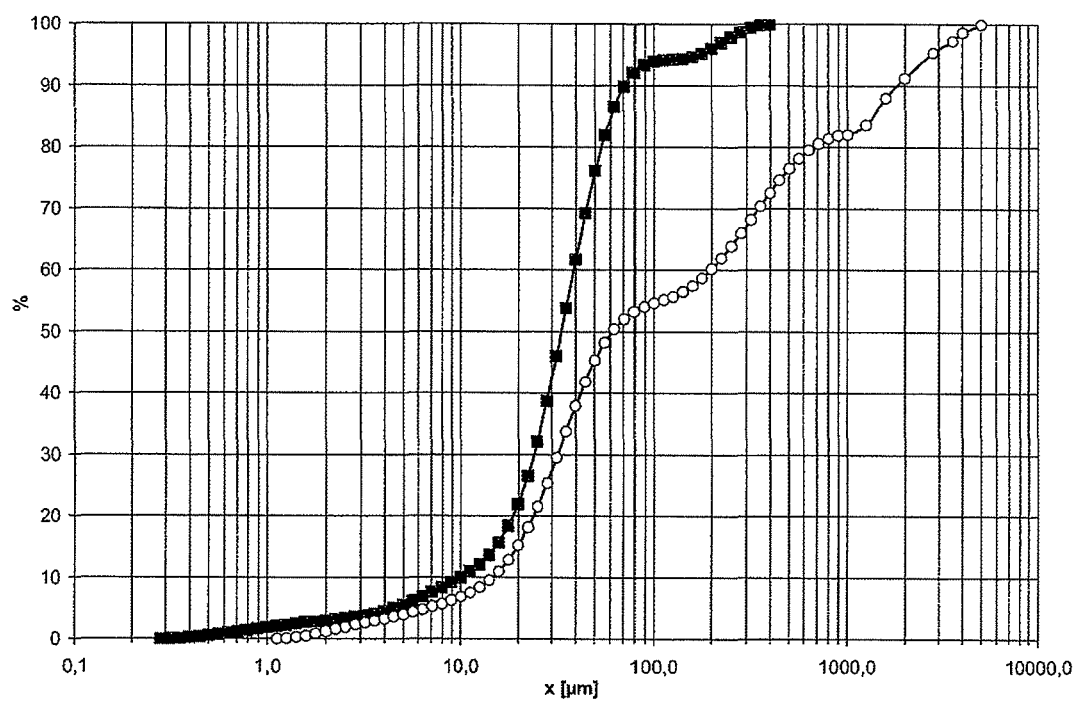

PROCESS FOR PREPARING POROUS METAL-ORGANIC FRAMEWORKS BASED ON ALUMINUM FUMARATE

CROSS-REFERENCE TO RELATED APPLICATIONS

This application claims the benefit under 35 U.S.C. §119(e) of U.S. Provisional Patent Application No. 61/387,991, filed Sep. 30, 2010, which is incorporated herein by reference in its entirety.

FIELD

The present invention relates to a process for preparing porous metal-organic frameworks.

BACKGROUND

Porous metal-organic frameworks are known in the prior art and form an interesting class of substances which can be an alternative to organic zeolites for various applications.

Numerous processes have been developed for preparing such porous metal-organic frameworks. Typically, a metal salt is reacted with the at least bidentate organic compound, for example a dicarboxylic acid, in a suitable solvent under superatmospheric pressure and elevated temperature.

However, difficulties frequently occur here. One problem can be that, owing to the use of a metal salt, the counterion to the metal cation remaining in the reaction medium after formation of the metal-organic framework (for example nitrate) has to be separated from the framework.

The use of high pressures and temperatures places severe demands on the synthesis apparatus for preparing a porous metal-organic framework. Usually, only a batch synthesis in comparatively small apparatuses is possible and has been described. A scale-up is found to be very complicated.

A further difficulty is that, depending on the metal and organic compound used for preparing the framework, it is not possible to carry over the reaction conditions readily. Such a case occurs, for example, when the metal component of the metal-organic framework is a main group metal of the second or third main group of the Periodic Table. Here, significantly different reaction conditions compared to analogous frameworks in which the metal component is a transition metal, for example zinc or copper, are sometimes employed for the preparation.

Such porous metal-organic frameworks, which can have a main group metal of the second or third main group, also differ in respect of their properties from the abovementioned analogous frameworks, which could be a reason why modified preparative processes are frequently employed for this purpose in the prior art.

WO-A 2007/023134 describes the preparation of such metal-organic frameworks based on main group metals. Here, preparation in a nonaqueous medium is disclosed. Although the synthesis proposed brings advantages, the use of organic solvents as reaction medium remains problematical, in particular for reactions of relatively large quantities of starting materials.

WO-A 2007/118841 likewise describes the preparation of a framework based on aluminum fumarate in organic solvents.

Apart from the problems associated with the use of organic solvents for health and environmental reasons, the processes disclosed in the prior art have conditions which tend to be unsuitable for production on an industrial scale and also in respect of characteristic parameters such as the space-time yield.

There is therefore a need for improved processes which, in particular, are suitable for industrial or large-scale production.

SUMMARY

Provided is a process for preparing a porous metal-organic framework, wherein the metal-organic framework comprises at least one at least bidentate organic compound coordinated to at least one metal ion, and wherein the at least one metal ion is based on an aluminum ion and the at least one at least bidentate organic compound is based on fumaric acid. The method comprises reacting at least one aluminum compound with fumaric acid in an alkaline aqueous medium, optionally in the presence of at least one base, at a temperature having a range of from 20° C. to 100° C. at an absolute pressure of not more than 2 bar for from 0.2 to 4 hours.

BRIEF DESCRIPTION OF THE FIGURE

FIG. 1 is a graphical distribution showing the particle size distribution of framework of two examples formed in accordance with one or more embodiments of the invention.

DETAILED DESCRIPTION

In accordance with one or more embodiment, provided are processes, which are suitable for the industrial or large-scale production of porous metal-organic frameworks.

One aspect of the invention relates to a process for preparing a porous metal-organic framework comprising at least one at least bidentate organic compound coordinated to at least one metal ion, where the at least one metal ion is based on an aluminum ion and the at least one at least bidentate organic compound is based on fumaric acid, which comprises the step reaction of at least one aluminum compound with at least fumaric acid in an alkaline aqueous medium, optionally in the presence of at least one base, at a temperature in the range from 20° C. to 100° C. at an absolute pressure of not more than 2 bar for from 0.2 to 4 hours.

It has surprisingly been found that high space-time yields can be achieved when the abovementioned features of the process of the invention are adhered to. It is particularly surprising here that the frameworks obtained can be obtained not only virtually quantitatively but also with very good specific surface areas.

The porous metal-organic framework prepared by the process of the invention comprises at least one metal ion which is an aluminum ion. However, it is likewise possible for more than one metal ion to be present in the porous metal-organic framework. These one or more metal ions other than aluminum can be located in the pores of the metal-organic framework or participate in the formation of the lattice of the framework. In the latter case, the at least one at least bidentate organic compound or a further at least bidentate organic compound would likewise be bound to such a metal ion.

Here, every metal ion which is suitable as part of the porous metal-organic framework is possible in principle. If more than one metal ion is comprised in the porous metal-organic framework, these can be present in a stoichiometric or nonstoichiometric amount. If coordination sites are occupied by a further metal ion and this is present in a nonstoichiometric ratio to the abovementioned metal ion, such a porous metal-organic framework can be considered to be a doped framework. The preparation of such doped metal-organic frameworks in general is described in EP-A 1 785 428. For the purposes of the present invention, a corresponding inventive preparation can be carried out by means of these preparative processes.

The porous metal-organic framework preferably has only one metal ion.

In addition, the porous metal-organic framework can be impregnated by a further metal in the form of a metal salt after the reaction according to the process of the invention. One method of carrying out the impregnation is described, for example, in EP-A 1070538.

If a further metal ion is present in a stoichiometric ratio to the aluminum ion, mixed metallic frameworks are present. Here, the further metal ion can participate or not participate in formation of the framework.

The framework is preferably made up of only aluminum ions and the at least one at least bidentate organic compound.

In addition, the porous metal-organic framework comprises at least one at least bidentate organic compound based on fumaric acid.

For the purposes of the present invention, the term "based" refers to fumaric acid or the anion thereof, preferably only to the anion thereof.

The metal-organic framework can also comprise one or more further at least bidentate organic compounds.

These one or more further at least bidenate organic compounds are preferably derived from a dicarboxylic, tricarboxylic or tetracarboxylic acid. Other at least bidentate organic compounds can also participate in the formation of the framework. However, it is likewise possible for organic compounds which are not at least bidentate also to be comprised in the framework. These can be derived, for example, from a monocarboxylic acid.

For the purposes of the present invention, the term "derived" means that the dicarboxylic, tricarboxylic or tetracarboxylic acid can be present in partially deprotonated or completely deprotonated form in the framework. Furthermore, the dicarboxylic, tricarboxylic or tetracarboxylic acid can comprise a substituent or a plurality of independent substituents. Examples of such substituents are —OH, —NH$_2$, —OCH$_3$, —CH$_3$, —NH(CH$_3$), —N(CH$_3$)$_2$, —CN and halides. Furthermore, the term "derived" as used for the purposes of the present invention means that the dicarboxylic, tricarboxylic or tetracarboxylic acid can also be present in the form of the corresponding sulfur analogues. Sulfur analogues are the functional groups —C(=O)SH and the tautomer thereof and C(=S)SH, which can be used instead of one or more carboxylic acid groups. Furthermore, the term "derived" as used for the purposes of the present invention means that one or more carboxylic acid functions can be replaced by a sulfonic acid group (—SO$_3$H). In addition, a sulfonic acid group can likewise be present in addition to the 2, 3 or 4 carboxylic acid functions.

The dicarboxylic, tricarboxylic or tetracarboxylic acid has, in addition to the abovementioned functional groups, an organic skeleton or an organic compound to which these are bound. Here, the abovementioned functional groups can in principle be bound to any suitable organic compound as long as it is ensured that the organic compound bearing these functional groups is suitable for forming the coordinate bond for producing the framework.

The organic compounds are preferably derived from a saturated or unsaturated aliphatic compound or an aromatic compound or a both aliphatic and aromatic compound.

The aliphatic compound or the aliphatic part of the both aliphatic and aromatic compound can be linear and/or branched and/or cyclic, with a plurality of rings per compound also being possible. The aliphatic compound or the aliphatic part of the both aliphatic and aromatic compound more preferably comprises from 1 to 18, more preferably from 1 to 14, more preferably from 1 to 13, more preferably from 1 to 12, more preferably from 1 to 11 and particularly preferably from 1 to 10, carbon atoms, for example 1, 2, 3, 4, 5, 6, 7, 8, 9 or 10 carbon atoms. Particular preference is given here to, inter alia, methane, adamantane, acetylene, ethylene or butadiene.

The aromatic compound or the aromatic part of the both aromatic and aliphatic compound can have one or more rings, for example two, three, four or five rings, with the rings being able to be present separately from one another and/or at least two rings being able to be present in condensed form. The aromatic compound or the aromatic part of the both aliphatic and aromatic compound particularly preferably has one, two or three rings, with one or two rings being particularly preferred. Each ring of said compound can independently comprise at least one heteroatom such as N, O, S, B, P, Si, preferably N, O and/or S. The aromatic compound or the aromatic part of the both aromatic and aliphatic compound more preferably comprises one or two C$_6$ rings, with the two rings being present either separately or in condensed form. Particular mention may be made of benzene, naphthalene and/or biphenyl and/or bipyridyl and/or pyridyl as aromatic compounds.

The at least bidentate organic compound is more preferably an aliphatic or aromatic, acyclic or cyclic hydrocarbon having from 1 to 18, preferably from 1 to 10 and in particular 6, carbon atoms and having exclusively 2, 3 or 4 carboxyl groups as functional groups.

For example, the at least bidentate organic compound is derived from a dicarboxylic acid such as oxalic acid, succinic acid, tartaric acid, 1,4-butanedicarboxylic acid, 1,4-butenedicarboxylic acid, 4-oxopyran-2,6-dicarboxylic acid, 1,6-hexanedicarboxylic acid, decanedicarboxylic acid, 1,8-heptadecanedicarboxylic acid, 1,9-heptadecanedicarboxylic acid, heptadecanedicarboxylic acid, acetylenedicarboxylic acid, 1,2-benzenedicarboxylic acid, 1,3-benzenedicarboxylic acid, 2,3-pyridinedicarboxylic acid, pyridine-2,3-dicarboxylic acid, 1,3-butadiene-1,4-dicarboxylic acid, 1,4-benzenedicarboxylic acid, p-benzenedicarboxylic acid, imidazole-2,4-dicarboxylic acid, 2-methylquinoline-3,4-dicarboxylic acid, quinoline-2,4-dicarboxylic acid, quinoxaline-2,3-dicarboxylic acid, 6-chloroquinoxaline-2,3-dicarboxylic acid, 4,4'-diaminophenylmethane-3,3'-dicarboxylic acid, quinoline-3,4-dicarboxylic acid, 7-chloro-4-hydroxyquinoline-2,8-dicarboxylic acid, di imidedicarboxylic acid, pyridine-2,6-dicarboxylic acid, 2-methylimidazole-4,5-dicarboxylic acid, thiophene-3,4-dicarboxylic acid, 2-isopropylimidazole-4,5-dicarboxylic acid, tetrahydropyran-4,4-dicarboxylic acid, perylene-3,9-dicarboxylic acid, perylenedicarboxylic acid, Pluriol E 200-dicarboxylic acid, 3,6-dioxaoctanedicarboxylic acid, 3,5-cyclohexadiene-1,2-dicarboxylic acid, octanedicarboxylic acid, pentane-3,3-carboxylic acid, 4,4'-diamino-1,1'-biphenyl-3,3'-dicarboxylic acid, 4,4'-diaminobiphenyl-3,3'-dicarboxylic acid, benzidine-3,3'-dicarboxylic acid, 1,4-bis(phenylamino)benzene-2,5-dicarboxylic acid, 1,1'-binaphthyldicarboxylic acid, 7-chloro-8-methylquinoline-2,3-dicarboxylic acid, 1-anilinoanthraquinone-2,4'-dicarboxylic acid, polytetrahydrofuran 250-dicarboxylic acid, 1,4-bis(carboxymethyl)piperazine-2,3-dicarboxylic acid, 7-chloroquinoline-3,8-dicarboxylic acid, 1-(4-carboxy) phenyl-3-(4-chloro)phenylpyrazoline-4,5-dicarboxylic acid, 1,4,5,6,7,7-hexachloro-5-norbornene-2,3-dicarboxylic acid, phenylindanedicarboxylic acid, 1,3-dibenzyl-2-oxoimidazolidine-4,5-dicarboxylic acid, 1,4-cyclohexanedicarboxylic acid, naphthalene-1,8-dicarboxylic acid, 2-benzoylbenzene-1,3-dicarboxylic acid, 1,3-dibenzyl-2-oxoimidazolidine-4,5-cis-dicarboxylic acid, 2,2'-biquinoline-4,4'-dicarboxylic acid, pyridine-3,4-dicarboxylic acid, 3,6,9-trioxaundecanedicarboxylic acid, hydroxybenzophenonedicarboxylic acid, Pluriol E 300-dicarboxylic acid, Pluriol E 400-dicarboxylic acid, Pluriol E 600-dicarboxylic acid, pyrazole-3,4-dicarboxylic acid, 2,3-pyrazinedicarboxylic acid, 5,6-dimethyl-2,3-pyrazinedicarboxylic acid, bis(4-aminophenyl)ether diimide-dicarboxylic acid, 4,4'-diaminodiphenylmethane diimide-dicarboxylic acid, bis(4-aminophenyl)sulfone diimide-dicarboxylic acid, 1,4-naphthalenedicarboxylic acid, 2,6-naphthalene-dicarboxylic acid, 1,3-adamantanedicarboxylic acid, 1,8-naphthalenedicarboxylic acid, 2,3-naphthalenedicarboxylic acid, 8-methoxy-2,3-naphthalenedicarboxylic acid, 8-nitro-2,3-naphthalenecarboxylic acid, 8-sulfo-2,3-naphthalenedicarboxylic acid, anthracene-2,3-dicarboxylic acid, 2',3'-diphenyl-p-terphenyl-4,4''-dicarboxylic acid, (diphenyl ether)-4,4'-dicarboxylic acid, imidazole-4,5-dicarboxylic acid, 4(1H)-oxothiochromene-2,8-dicarboxylic acid, 5-tert-butyl-1,3-benzenedicarboxylic acid, 7,8-quinolinedicarboxylic acid, 4,5-imidazoledicarboxylic acid, 4-cyclohexene-1,2-dicarboxylic acid, hexatriacontanedicarboxylic acid, tetradecanedicarboxylic acid, 1,7-heptanedicarboxylic acid, 5-hydroxy-1,3-benzenedicarboxylic acid, 2,5-dihydroxy-1,4-benzenedicarboxylic acid, pyrazine-2,3-dicarboxylic acid, furan-2,5-dicarboxylic acid, 1-nonene-6,9-dicarboxylic acid, eicosenedicarboxylic acid, 4,4'-dihydroxy-diphenylmethane-3,3'-dicarboxylic acid, 1-amino-4-methyl-9,10-dioxo-9,10-dihydroanthracene-2,3-dicarboxylic acid, 2,5-pyridinedicarboxylic acid, cyclohexene-2,3-dicarboxylic acid, 2,9-dichlorofluorubin-4,11-dicarboxylic acid, 7-chloro-3-methylquinoline-6,8-dicarboxylic acid, 2,4-dichlorobenzophenone-2',5'-dicarboxylic acid, 1,3-benzenedicarboxylic acid, 2,6-pyridinedicarboxylic acid, 1-methylpyrrol-3,4-dicarboxylic acid, 1-benzyl-1H-pyrrol-3,4-dicarboxylic acid, anthraquinone-1,5-dicarboxylic acid, 3,5-pyrazoledicarboxylic acid, 2-nitrobenzene-1,4-dicarboxylic acid, heptane-1,7-dicarboxylic acid, cyclobutane-1,1-dicarboxylic acid, 1,14-tetradecanedicarboxylic acid, 5,6-dehydronorbornane-2,3-dicarboxylic acid, 5-ethyl-2,3-pyridinedicarboxylic acid or camphordicarboxylic acid.

The at least bidentate organic compound is even more preferably one of the dicarboxylic acids mentioned above by way of example as such.

For example, the at least bidentate organic compound can be derived from a tricarboxylic acid such as 2-Hydroxy-1,2,3-propanetricarboxylic acid, 7-chloro-2,3,8-quinolinetricarboxylic acid, 1,2,3-, 1,2,4-benzenetricarboxylic acid, 1,2,4-butanetricarboxylic acid, 2-phosphono-1,2,4-butanetricarboxylic acid, 1,3,5-benzenetricarboxylic acid, 1-hydroxy-1,2,3-propanetricarboxylic acid, 4,5-dihydroxy-4,5-dioxo-1H-pyrrolo[2,3-F]quinoline-2,7,9-tricarboxylic acid, 5-acetyl-3-amino-6-methylbenzene-1,2,4-tricarboxylic acid, 3-amino-5-benzoyl-6-methylbenzene-1,2,4-tricarboxylic acid, 1,2,3-propanetricarboxylic acid or aurintricarboxylic acid.

The at least bidentate organic compound is even more preferably one of the tricarboxylic acids mentioned above by way of example as such.

Examples of an at least bidentate organic compound which is derived from a tetracarboxylic acid are 1,1-Dioxidoperylo[1,12-BCD]thiophene-3,4,9,10-tetracarboxylic acid, perylenetetracarboxylic acids such as perylene-3,4,9,10-tetracarboxylic acid or (perylene-1,12-sulfone)-3,4,9,10-tetracarboxylic acid, butanetetracarboxylic acids such as 1,2,3,4-butanetetracarboxylic acid or meso-1,2,3,4-butanetetracarboxylic acid, decane-2,4,6,8-tetracarboxylic acid, 1,4,7,10,13,16-hexaoxacyclooctadecane-2,3,11,12-tetracarboxylic acid, 1,2,4,5-benzenetetracarboxylic acid, 1,2,11,12-dodecanetetracarboxylic acid, 1,2,5,6-hexanetetracarboxylic acid, 1,2,7,8-octanetetracarboxylic acid, 1,4,5,8-naphthalenetetracarboxylic acid, 1,2,9,10-decanetetracarboxylic acid, benzophenonetetracarboxylic acid, 3,3',4,4'-benzophenonetetracarboxylic acid, tetrahydrofurantetracarboxylic acid or cyclopentantetracarboxylic acids such as cyclopentane-1,2,3,4-tetracarboxylic acid.

The at least bidentate organic compound is even more particularly preferably one of the tetracarboxylic acids mentioned above by way of example as such.

Very particular preference is given to using optionally at least monosubstituted aromatic dicarboxylic, tricarboxylic or tetracarboxylic acids having one, two, three, four or more rings, where each of the rings can comprise at least one heteroatom, in which case two or more rings can comprise identical or different heteroatoms. Preference is given to, for example, monocyclic dicarboxylic acids, monocyclic tricarboxylic acids, monocyclic tetracarboxylic acids, bicyclic dicarboxylic acids, bicyclic tricarboxylic acids, bicyclic tetracarboxylic acids, tricyclic dicarboxylic acids, tricyclic tricarboxylic acids, tricyclic tetracarboxylic acids, tetracyclic dicarboxylic acids, tetracyclic tricarboxylic acids and/or tetracyclic tetracarboxylic acids. Suitable heteroatoms are, for example, N, O, S, B, P, and preferred heteroatoms are N, S and/or O. A suitable substituent here is, inter alia, —OH, a nitro group, an amino group or an alkyl or alkoxy group.

Particular preference is given to using acetylenedicarboxylic acid (ADC), camphordicarboxylic acid, fumaric acid, succinic acid, benzenedicarboxylic acids, naphthalenedicarboxylic acids, biphenyldicarboxylic acids such as 4,4'-biphenyldicarboxylic acid (BPDC), pyrazinedicarboxylic acids such as 2,5-pyrazinedicarboxylic acid, bipyridinedicarboxylic acids such as 2,2'-bipyridinedicarboxylic acids such as 2,2'-bipyridine-5,5'-dicarboxylic acid, benzenetricarboxylic acids such as 1,2,3-, 1,2,4-benzenetricarboxylic acid or 1,3,5-benzenetricarboxylic acid (BTC), benzenetetracarboxylic acid, adamantanetetracarboxylic acid (ATC), adamantanedibenzoate (ADB) benzenetribenzoate (BTB), methanetetrabenzoate (MTB), adamantanetetrabenzoate or dihydroxyterephthalic acids such as 2,5-dihydroxyterephthalic acid (DHBDC) as at least bidentate organic compounds.

Very particular preference is given to, inter alia, phthalic acid, isophthalic acid, terephthalic acid, 2,6-naphthalenedicarboxylic acid, 1,4-naphthalenedicarboxylic acid, 1,5-naphthalenedicarboxylic acid, 1,2,3-benzenetricarboxylic acid, 1,2,4-benzenetricarboxylic acid, 1,3,5-benzenetricarboxylic acid or 1,2,4,5-benzenetetracarboxylic acid.

Apart from these at least bidentate organic compounds, the metal-organic framework can also comprise one or more monodentate ligands and/or one or more bidentate ligands which are not derived from a dicarboxylic, tricarboxylic or tetracarboxylic acid.

However, the porous metal-organic framework preferably has only one at least bidentate organic compound (fumaric acid).

A porous metal-organic framework made up of Al(III) ions to which fumarate ions are coordinated to form a framework structure is preferred. Such a material is described in WO-A 2007/118841.

The metal-organic frameworks obtained by the process of the invention comprise pores, in particular micropores and/or mesopores. Micropores are defined as pores having a diameter of 2 nm or less and mesopores are defined by a diameter in the range from 2 to 50 nm, in each case corresponding to the definition given in Pure Applied Chem. 57 (1985), pages 603-619, in particular on page 606. The presence of micropores and/or mesopores can be checked by means of sorption measurements which determine the uptake capacity of the metal-organic frameworks for nitrogen at 77 kelvin in accordance with DIN 66131 and/or DIN 66134.

The specific surface area calculated according to the Langmuir model (DIN 66131, 66134) of the metal-organic framework in powder form is preferably greater than 800 $m^2/g$, more preferably above 900 $m^2/g$, more preferably greater than 1000 $m^2/g$, even more preferably greater than 1100 $m^2/g$.

Shaped bodies composed of metal-organic frameworks can have a lower specific surface area.

The metal-organic framework can be present in powder form or as agglomerate. The framework can be used as such or is converted into a shaped body. The production of shaped bodies from metal-organic frameworks is described, for example, in WO-A 03/102000.

The at least one aluminum compound is preferably an inorganic salt, in particular a halide, sulfide, the salt of an inorganic oxygen-comprising acid, optionally in the form of a hydrate or a mixture thereof.

A halide is, for example, chloride, bromide or iodide.

An inorganic oxygen-comprising acid is, for example, sulfuric acid, sulfurous acid, phosphoric acid or nitric acid.

Particular preference is given to aluminum sulfate, in particular in the form of its octadecahydrate or tetradecahydrate.

As at least one aluminum compound, it is also possible to use an aluminate such as an alkali metal aluminate, e.g. $NaAlO_2$. Since this has basic properties, the presence of a base in the reaction can be dispensed with. However, it is also possible to use an additional base.

The reaction in the process of the invention is carried out in the presence of an aqueous solvent (aqueous medium) having a basic reaction. Here, the water content is, if mixtures are used, preferably more than 50% by weight, more preferably more than 60% by weight, even more preferably more than 70% by weight, even more preferably more than 80% by weight, even more preferably more than 90% by weight, even more preferably more than 95% by weight, even more preferably more than 99% by weight. In particular, the aqueous solvent consists exclusively of water.

A basic medium (a basic reaction) means, according to the general meaning of the term, a pH of greater than 7.

This can, for example, be achieved by the at least one aluminum compound used having a sufficiently basic reaction in order to produce a basic aqueous medium. In addition or as an alternative, i.e. when the at least one aluminum compound does not have a basic reaction or does not have a sufficiently basic reaction, a base can be used in the reaction.

The reaction is typically carried out in water as solvent in the presence of a base. This ensures, in particular, that when an in particular polybasic carboxylic acid is used as at least bidentate organic compound, this carboxylic acid is sufficiently soluble in water.

Preference is given to using an alkali metal hydroxide or a mixture of a plurality of different alkali metal hydroxides as base. Examples are, in particular, sodium hydroxide and potassium hydroxide. However, further inorganic hydroxides or carbonates or organic bases such as amines are also conceivable. Sodium hydroxide is particularly preferred.

The reaction is carried out at a pressure of not more than 2 bar (absolute). However, the pressure is preferably not more than 1230 mbar (absolute). In particular, the reaction is carried out at atmospheric pressure. However, slightly superatmospheric or subatmospheric pressure can occur as a result of the apparatus. For the purposes of the present invention, the term "atmospheric pressure" therefore refers to the pressure range given by the actual prevailing atmospheric pressure±150 mbar.

The reaction can be carried out at room temperature (20° C.). However, the reaction can take place at temperatures above room temperature. In any case, the reaction is carried out in the range from 20° C. to 100° C. A range from 40° C. to 80° C. is preferred. Greater preference is given to a range from 50° C. to 70° C.

Furthermore, it is advantageous for the reaction to be carried out with mixing of the reaction mixture. The reaction can therefore take place with stirring, which is also advantageous in the case of a scale-up. More effective mixing can be carried out by pumped circulation during the reaction. This makes continuous operation of the process of the invention possible.

To achieve a high space-time yield, the reaction takes place for from 0.2 hour to 4 hours. The reaction is preferably carried out for from 0.2 hour to 2 hours. The reaction is more preferably carried out for from 0.2 hour to 1 hour. The reaction is more preferably carried out for from 0.2 hour to 0.5 hour.

This enables space-time yields of more than 3000 kg/($m^3 \cdot$day) to be achieved at high specific surface areas.

The molar ratio of aluminum compound used for the reaction, based on aluminum, to fumaric acid used is preferably in the range from 0.66 to 1.50. Greater preference is given to a range from 0.75 to 1.25, even more preferably from 0.9 to 1.1. Particular preference is given to a molar ratio of 1.

The molar ratio of fumaric acid used for the reaction to base used, if the latter is used, is preferably in the range from 0.25 to 0.67. Greater preference is given to a range from 0.25 to 0.5, even more preferably from 0.3 to 0.4. Particular preference is given to a molar ratio of 0.33.

The weight ratio of total aluminum compound used for the reaction and fumaric acid used to the aqueous medium used is preferably in the range from 7% by weight to 28% by weight. Greater preference is given to a range from 10% by weight to 20% by weight, even more preferably from 12% by weight to 16% by weight. Particular preference is given to 14% by weight.

The reaction mixture obtained after the reaction is preferably subjected to spray drying.

Spray drying makes it possible to obtain a material which has an improved, i.e. narrower, pore distribution.

The porous metal-organic framework obtained can be subjected to calcination. The calcination can be carried out as an alternative to or in addition to spray drying.

Accordingly, the process step of the reaction of the at least one metal compound with the at least one at least bidentate organic compound is accordingly followed by a calcination step which is preferably carried out after any spray drying is carried out. The temperature set in the calcination (with or without spray drying step) is typically greater than 150° C., preferably from 200° C. to 400° C., more preferably from 250° C. to 400° C., even more preferably from 300° C. to 400° C.

The calcination step can remove the at least bidentate organic compound present in the pores.

FIG. 1 shows the particle size distribution of framework which has not been spray dried from example 5 (curve with circles) and spray-dried framework from example 6 (curve with squares). The curves show the cumulative particle sizes in % as a function of the particle size x in μm.

EXAMPLES

Example 1

Al-fumarate MOF synthesis (0.17 h, RT)

Experimental Method:

| Starting material | Molar | Calculated | Experimental |
|---|---|---|---|
| 1) Fumaric acid | 0.209 mol | 24.3 g | 24.3 g |
| 2) Sodium hydroxide | 0.63 mol | 25.2 g | 25.2 g |
| 3) Aluminum sulfate*18 water | 0.105 mol | 70.0 g | 70.0 g |
| 4) Water | 36.66 mol | 660.0 g | 660.0 g |

In a glass beaker, aluminum sulfate was dissolved in 300 g of water at room temperature ("RT"). 409 g of a solution composed of fumaric acid, sodium hydroxide and 360 g of water was pumped into this solution over a period of 10 minutes while stirring. A white suspension was formed. This was filtered and the solid was washed once with 100 ml of water and 3 times with 50 ml of water. The filter cake was dried overnight at 100° C. in air and subsequently dried overnight again at 130° C. in a vacuum drying oven.

Product weight: 26.2 g
Solids concentration of product: 3.4 wt %
Space-time yield: 4742 kg/m$^3$/day
Yield based on Al: 76 mol %
Analyses:
Surface area by the Langmuir method: 723 m$^2$/g
Chemical Analysis:
Al: 16.5 wt %

Example 2

Al-Fumarate MOF Synthesis (0.17 h, 60° C.)

Experimental Method:

| Starting material | Molar | Calculated | Experimental |
|---|---|---|---|
| 1) Fumaric acid | 0.209 mol | 24.3 g | 24.3 g |
| 2) Sodium hydroxide | 0.63 mol | 25.2 g | 25.2 g |
| 3) Aluminum sulfate*18 water | 0.105 mol | 70.0 g | 70.0 g |
| 4) Water | 36.66 mol | 660.0 g | 660.0 g |

In a glass beaker, aluminum sulfate was dissolved in 300 g of water at RT and heated to 60° C. 409 g of a solution (60° C.) composed of fumaric acid, sodium hydroxide and 360 g of water was pumped into this solution over a period of 10 minutes while stirring. A white suspension was formed. This was filtered and the solid was washed once with 100 ml of water and 3 times with 50 ml of water. The filter cake was dried overnight at 100° C. in air and subsequently dried overnight again at 130° C. in a vacuum drying oven.

Product weight: 29.5 g
Solids concentration of product: 3.8 wt %
Space-time yield: 5339 kg/m$^3$/day
Yield based on Al: 86 mol %
Analyses:
Surface area by the Langmuir method: 1140 m$^2$/g
Chemical Analysis:
Al: 16.6 wt %

Example 3

Al-Fumarate MOF Synthesis (0.27 h, 60° C.)

Experimental Method:

| Starting material | Molar | Calculated | Experimental |
|---|---|---|---|
| 1) Fumaric acid | 0.222 mol | 25.82 g | 25.82 g |
| 2) Sodium hydroxide | 0.668 mol | 26.71 g | 26.71 g |
| 3) Aluminum sulfate*18 water | 0.105 mol | 70.0 g | 70.0 g |
| 4) Water | 37.8 mol | 681.6 g | 681.6 g |

In a glass beaker, aluminum sulfate was dissolved in 300 g of water at RT and heated to 60° C. 434.1 g of a solution (60° C.) composed of fumaric acid, sodium hydroxide and 381.6 g of water was pumped into this solution over a period of 16 minutes while stirring. A white suspension was formed. This was filtered and the solid was washed once with 100 ml of water and 3 times with 50 ml of water. The filter cake was dried overnight at 100° C. in air and subsequently dried overnight again at 130° C. in a vacuum drying oven.

Product weight: 32.7 g
Solids concentration of product: 4.1 wt %
Space-time yield: 3615 kg/m$^3$/day
Yield based on Al: 97.5 mol %
Analyses:
Surface area by the Langmuir method: 1135 m$^2$/g
Chemical Analysis:
Al: 16.9 wt %

Example 4

Al-Fumarate MOF Synthesis (0.5 h, 60° C.)

Experimental Method:

| Starting material | Molar | Calculated | Experimental |
|---|---|---|---|
| 1. Fumaric acid | 0.211 mol | 24.47 g | 24.47 g |
| 2. Sodium hydroxide | 0.633 mol | 25.32 g | 25.32 g |
| 3. Aluminum sulfate*18 water | 0.105 mol | 70.0 g | 70.0 g |
| 4. Water | 36.8 mol | 661.7 g | 661.77 g |

In a glass beaker, aluminum sulfate was dissolved in 300 g of water and heated to 60° C. 411.5 g of a solution (60° C.) composed of fumaric acid, sodium hydroxide and 361.7 g of water was pumped into this solution over a period of 28 minutes while stirring. A white suspension was formed. This was filtered and the solid was washed once with 100 ml of water and 3 times with 50 ml of water. The filter cake was dried overnight at 100° C. in air and subsequently dried overnight again at 130° C. in a vacuum drying oven.

Product weight: 33.08 g
Solids concentration of product: 4.2 wt %
Space-time yield: 2032 kg/m$^3$/day
Yield based on Al: 98 mol %
Analyses:
Surface area by the Langmuir method: 1113 m$^2$/g
Chemical Analysis:
Al: 16.8 wt %

Example 5

Al-Fumaric Acid MOF without Spray Drying Step

|  | Molar mass | Batch |  |
|---|---|---|---|
| Fumaric acid | 116.07 g/mol | 111 mol | 12.9 kg |
| $Al_2(SO_4)_3 \times 18H_2O$ | 666.43 g/mol | 56 mol | 37.1 kg |
| Water | 18.02 g/mol | 19 423 mol | 350 kg |
| NaOH | 40.00 g/mol | 238 mmol | 9.5 kg |
| Temperature: |  | 60° C. |  |
| Duration: |  | 2 h feed, 2 h further stirring time |  |

Procedure:

1. Preparation of the solution to be added
2. 191 kg of deionized water were placed by direct introduction in a 0.4 m³ reactor.
3. 9.5 kg of sodium hydroxide pellets were introduced a little at a time at RT while stirring.
4. 12.9 kg of fumaric acid were added a little at a time to the previously prepared NaOH solution while stirring, completely dissolved.
5. Reaction procedure
6. 159 kg of deionized water from a direct line were placed in a 0.4 m³ reactor.
7. 37.1 kg of aluminum sulfate 18 hydrate were introduced a little at a time at RT while stirring.
8. Contents of the vessel were heated to 60° C. over a period of one hour while stirring.
9. The complete solution to be added (which was prepared in steps 2-5) was metered into the reaction vessel over a period of 2 hours. Reaction temperature: 60° C., further stirring time: 2 hours.
10. The suspension was filtered through a 160 l filter.
11. Washing of the filter cake
12. Washed 10 times with 50 liters each time of deionized water at RT.

Drying:
Starting weight: 1061 g;
At 100° C./72 hours in a convection drying oven; then at 150° C./72 hours in a vacuum drying oven
Product weight: 470 g;
Loss on drying: 55.7% by weight
Analyses:
Elemental analysis: Al 16.7% by weight
Surface area: 1294 m²/g by the Langmuir method
Bulk density: 471 g/l
Hg Porosimetry:
Total intrusion volume=1.7544 ml/g
Total pore area=217.924 m²/g
Average pore diameter (4V/A)=0.0322 μm

Example 6

Al-Fumaric Acid MOF with Spray Drying Step

Spray Drying:
The moist filter cake from example 5 was spray dried.
Spray drying was carried out in a conical laboratory fluidized-bed spray dryer which was operated as a spray tower. The suspension was sprayed from the top by means of a two-fluid nozzle. The fluidized bed was operated empty (i.e. powder formed was immediately taken off by means of a discharge screw). The spray tower was operated in countercurrent, with the nitrogen which served as drying gas being introduced from below via the fluidization plate. Spray drying was carried out in a conical laboratory fluidized-bed spray dryer which was operated as a spray tower. The suspension was sprayed from the top by means of a two-fluid nozzle.
Amount of solid sprayed: 12.64 kg.
Analyses (after Preactivation at 150° C./72 Hours in a Vacuum Drying Oven):
Elemental analysis: Al 16.5% by weight
Surface area: 1333 m²/g by the Langmuir method
Bulk density: 429 g/l
Hg Porosimetry:
Total intrusion volume=2.1009 ml/g
Total pore area=244.049 m²/g
Average pore diameter (4V/A)=0.0344 μm FIG. 1 shows the particle size distribution of framework which has not been spray dried and spray-dried framework from examples 5 and 6. A narrower particle size distribution is found for the spray-dried material.

The invention claimed is:

1. A process for preparing a porous metal-organic framework comprising at least one at least bidentate organic compound based on fumaric acid coordinated to at least one metal ion based on an aluminum ion, the method comprising:
reacting at least one aluminum compound with fumaric acid in an alkaline aqueous medium, optionally in the presence of at least one base, at a temperature having a range of from 20° C. to 100° C. at an absolute pressure of not more than 2 bar for from 0.2 to 4 hours to provide a reaction product.

2. The process according to claim 1, wherein the porous metal-organic framework has one metal ion.

3. The process according to claim 1, wherein the porous metal-organic framework has one at least bidentate organic compound.

4. The process according to claim 1, wherein the at least one aluminum compound is an inorganic salt.

5. The process according to claim 1, wherein the aqueous medium consists exclusively of water.

6. The process according to claim 1, wherein the reaction is carried out in the presence of a base.

7. The process according to claim 6, wherein the base is an alkali metal hydroxide or a mixture of a plurality of different alkali metal hydroxides.

8. The process according to claim 1, wherein the temperature is in the range of from 40° C. to 80° C.

9. The process according to claim 1, wherein the reaction is carried out under atmospheric pressure.

10. The process according to claim 1, wherein the reaction is carried out for from 0.2 to 2 hours.

11. The process according to claim 1, wherein the molar ratio of the aluminum compound used for the reaction, based on aluminum, to fumaric acid used is in the range of from 0.66 to 1.50.

12. The process according to claim 6, wherein the molar ratio of fumaric acid used for the reaction to base used is has a range of from 0.25 to 0.67.

13. The process according to claim 1, wherein the weight ratio of total aluminum compound used for the reaction and fumaric acid used to aqueous medium used is in the range of from 7% by weight to 28% by weight.

14. The process according to claim 1, further comprising spray drying the reaction product.

15. The process according claim 1, further comprising calcination of the reaction product.

16. The method of claim 1, further comprising impregnating the reaction product with a second metal in the form of a metal salt.

* * * * *